United States Patent
Hiroike

(10) Patent No.: US 9,192,350 B2
(45) Date of Patent: Nov. 24, 2015

(54) RADIATION IMAGING APPARATUS AND RADIATION IMAGING SYSTEM

(71) Applicant: CANON KABUSHIKI KAISHA, Tokyo (JP)

(72) Inventor: Taro Hiroike, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 229 days.

(21) Appl. No.: 13/864,528

(22) Filed: Apr. 17, 2013

(65) Prior Publication Data

US 2013/0279657 A1    Oct. 24, 2013

(30) Foreign Application Priority Data

Apr. 19, 2012    (JP) ................. 2012-096099

(51) Int. Cl.
*A61B 6/00* (2006.01)
*H05G 1/08* (2006.01)

(52) U.S. Cl.
CPC ............... *A61B 6/566* (2013.01); *A61B 6/4233* (2013.01); *A61B 6/4405* (2013.01); *A61B 6/54* (2013.01); *A61B 6/542* (2013.01); *A61B 6/56* (2013.01); *A61B 6/563* (2013.01); *H05G 1/08* (2013.01)

(58) Field of Classification Search
CPC ............ A61B 6/54; A61B 6/542; A61B 6/56; A61B 6/563; A61B 6/566
USPC .............................. 378/91, 96–98, 98.7, 98.8
See application file for complete search history.

(56) References Cited

U.S. PATENT DOCUMENTS

| | | | | |
|---|---|---|---|---|
| 6,442,238 B2* | 8/2002 | Meulenbrugge | ............ | 378/98.8 |
| 7,528,376 B2* | 5/2009 | Shoji | ........................ | 250/370.09 |
| 7,737,427 B2* | 6/2010 | Kito et al. | ..................... | 250/580 |
| 7,801,276 B2* | 9/2010 | Ohta et al. | .................... | 378/115 |
| 7,864,923 B2* | 1/2011 | Ohta et al. | .................... | 378/102 |
| 7,894,575 B2* | 2/2011 | Tsubota et al. | ................ | 378/96 |
| 7,991,119 B2* | 8/2011 | Yoshida et al. | .............. | 378/114 |
| 8,021,047 B2* | 9/2011 | Yoshida et al. | .............. | 378/207 |
| 8,053,727 B2* | 11/2011 | Nishino et al. | ............. | 250/336.1 |
| 8,213,573 B2* | 7/2012 | Liu et al. | ......................... | 378/62 |
| 8,229,202 B2* | 7/2012 | Kito et al. | ..................... | 382/132 |
| 8,264,543 B2* | 9/2012 | Harada et al. | ................ | 348/162 |
| 8,330,597 B2* | 12/2012 | Nishino et al. | ................ | 340/540 |
| 8,345,820 B2* | 1/2013 | Yoshida et al. | ................. | 378/62 |
| 8,358,740 B2* | 1/2013 | Nakatsugawa et al. | ....... | 378/116 |

(Continued)

FOREIGN PATENT DOCUMENTS

| | | | |
|---|---|---|---|
| JP | 2000107159 A | 4/2000 |
| JP | 2002125960 A | 5/2002 |

(Continued)

*Primary Examiner* — Allen C. Ho
(74) *Attorney, Agent, or Firm* — Canon USA Inc. IP Division

(57) ABSTRACT

A portable radiation imaging apparatus configured to wirelessly communicate with a radiation generation apparatus includes a radiation image sensor including a two-dimensional arrangement of a plurality of detection elements configured to detect a radiation generated by the radiation generation apparatus, a wireless communication unit configured to receive a generation condition of the radiation generated by the radiation generation apparatus, a storage unit configured to store the received generation condition and radiation image data obtained by the radiation image sensor in association with each other, and a housing configured to accommodate the radiation image sensor, the wireless communication unit, and the storage unit.

25 Claims, 11 Drawing Sheets

(56) References Cited

U.S. PATENT DOCUMENTS

| | | | |
|---|---|---|---|
| 8,363,786 B2 * | 1/2013 | Nakatsugawa et al. | 378/116 |
| 8,396,188 B2 * | 3/2013 | Liu et al. | 378/62 |
| 8,550,709 B2 * | 10/2013 | Nishino et al. | 378/207 |
| 8,576,087 B2 * | 11/2013 | Kamiya et al. | 340/687 |
| 8,654,925 B2 * | 2/2014 | Nishino | 378/98.5 |
| 8,654,926 B2 * | 2/2014 | Ohta et al. | 378/114 |
| 8,744,043 B2 * | 6/2014 | Ohta et al. | 378/62 |
| 8,792,612 B2 * | 7/2014 | Konishi | 378/62 |
| 8,831,177 B2 * | 9/2014 | Chung et al. | 378/97 |
| 8,885,795 B2 * | 11/2014 | Enomoto | 378/98.8 |
| 8,903,048 B2 * | 12/2014 | Kitano et al. | 378/115 |
| 9,001,972 B2 * | 4/2015 | Takahashi et al. | 378/98 |
| 2006/0008054 A1 * | 1/2006 | Ohara | 378/114 |

FOREIGN PATENT DOCUMENTS

| | | |
|---|---|---|
| JP | 2004180931 A | 7/2004 |
| JP | 2006025832 A | 2/2006 |
| JP | 2010075663 A | 4/2010 |
| JP | 2011212310 A | 10/2011 |
| JP | 2012035009 A | 2/2012 |

* cited by examiner

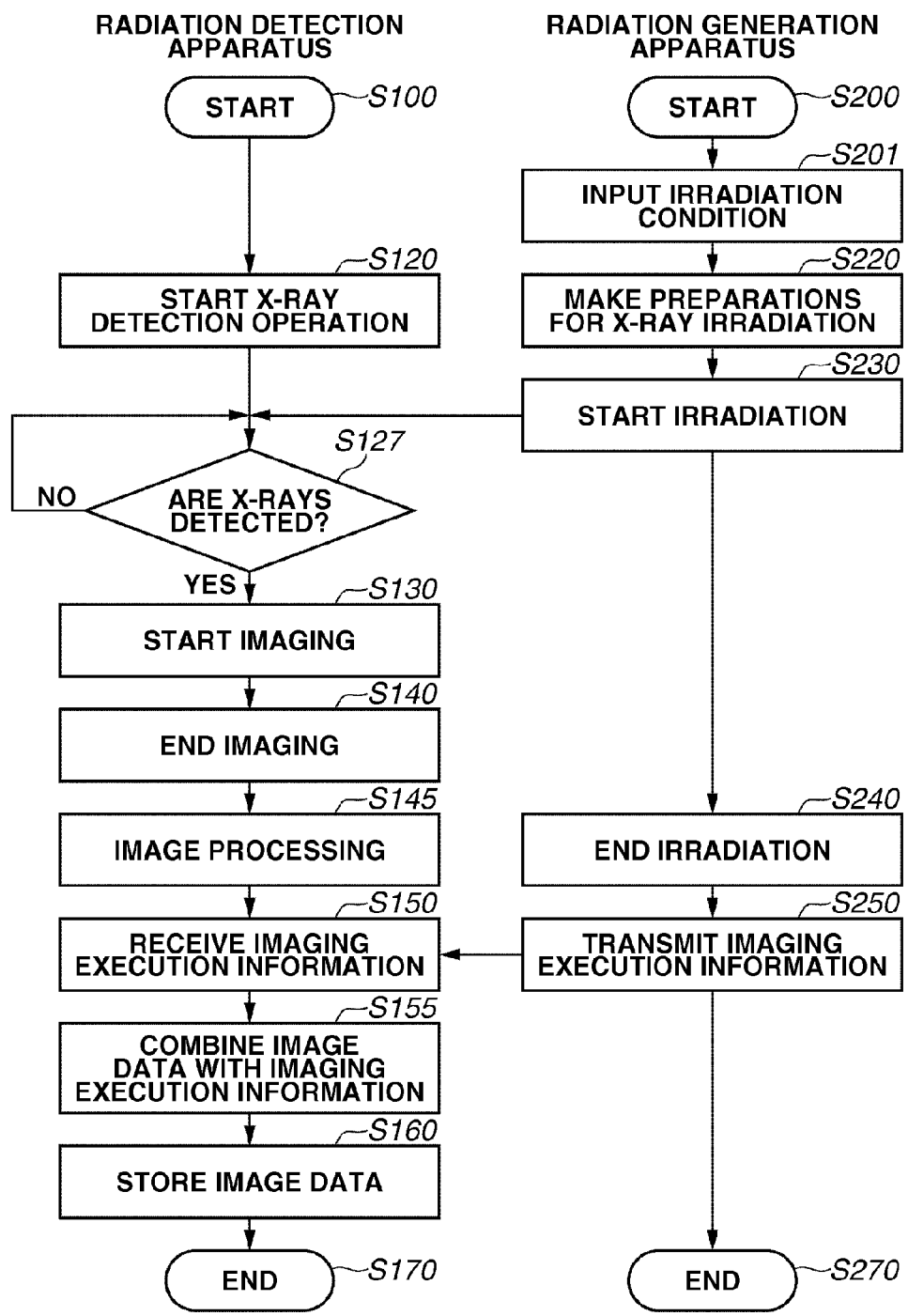

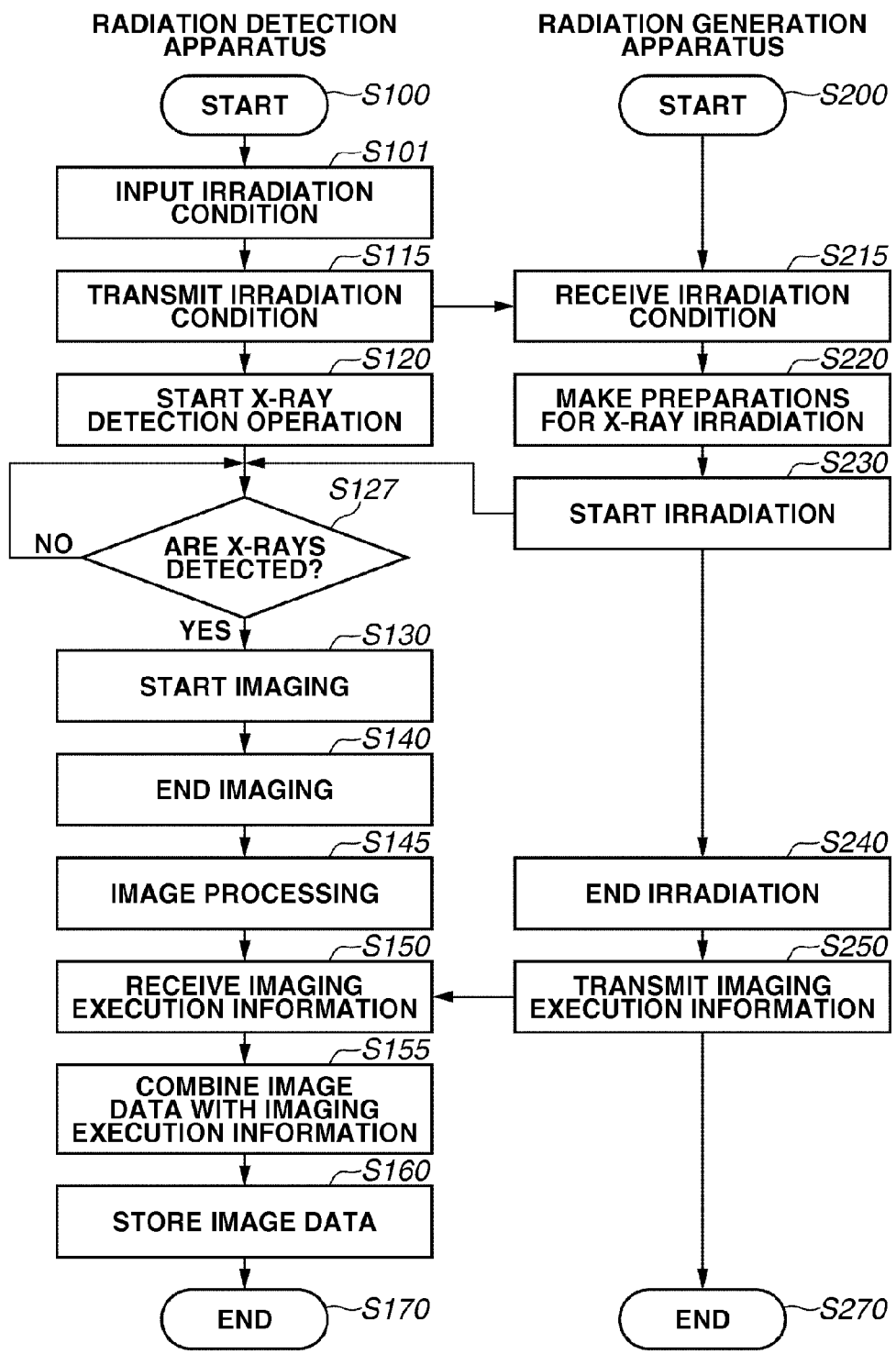

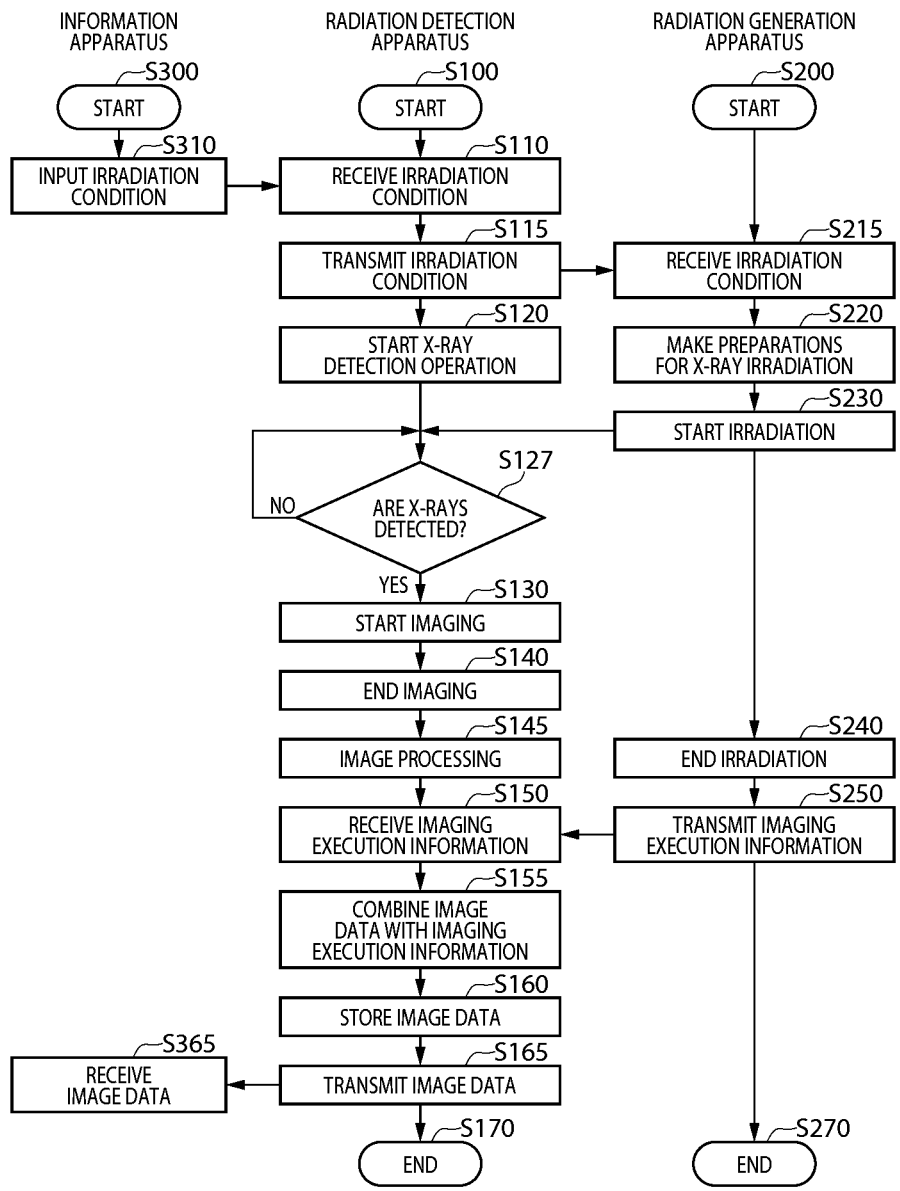

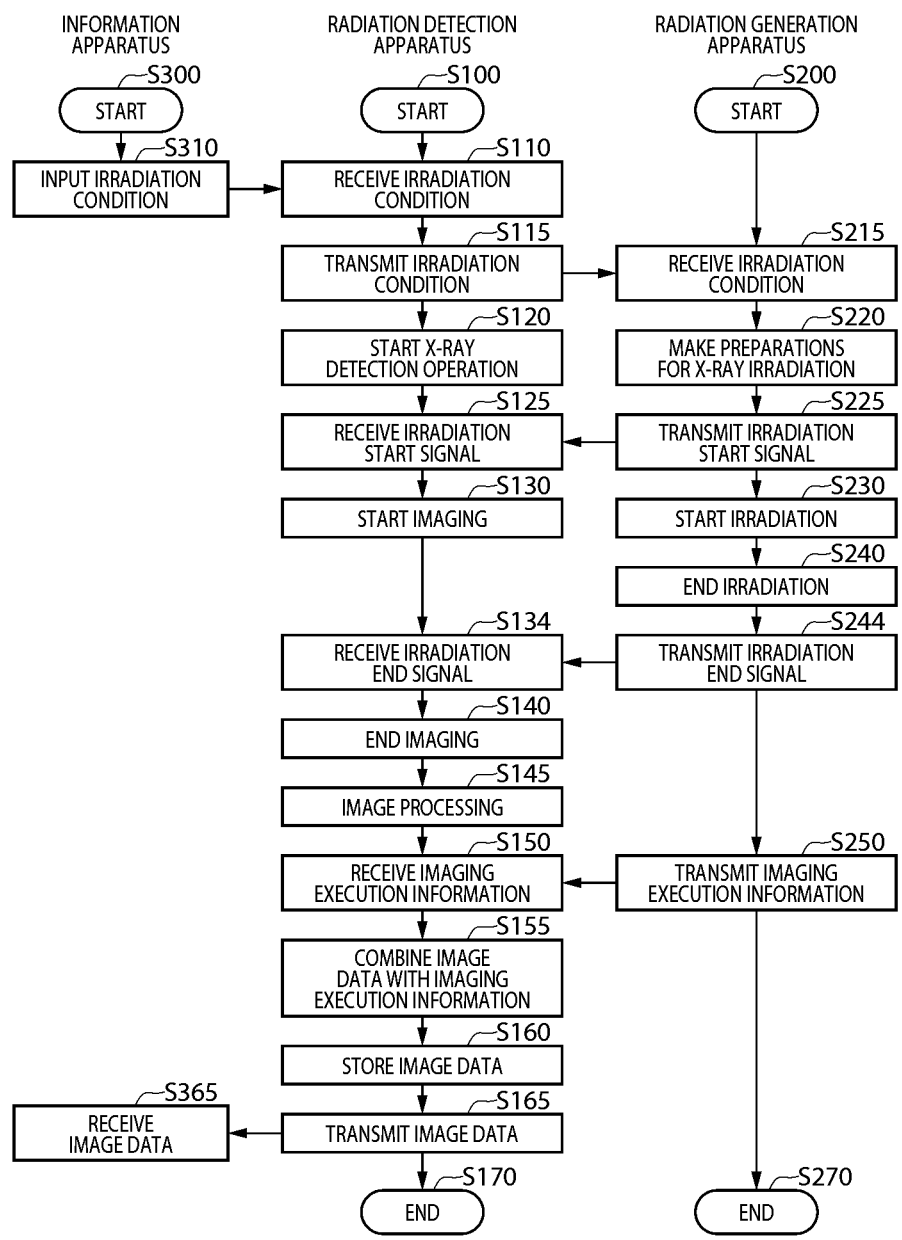

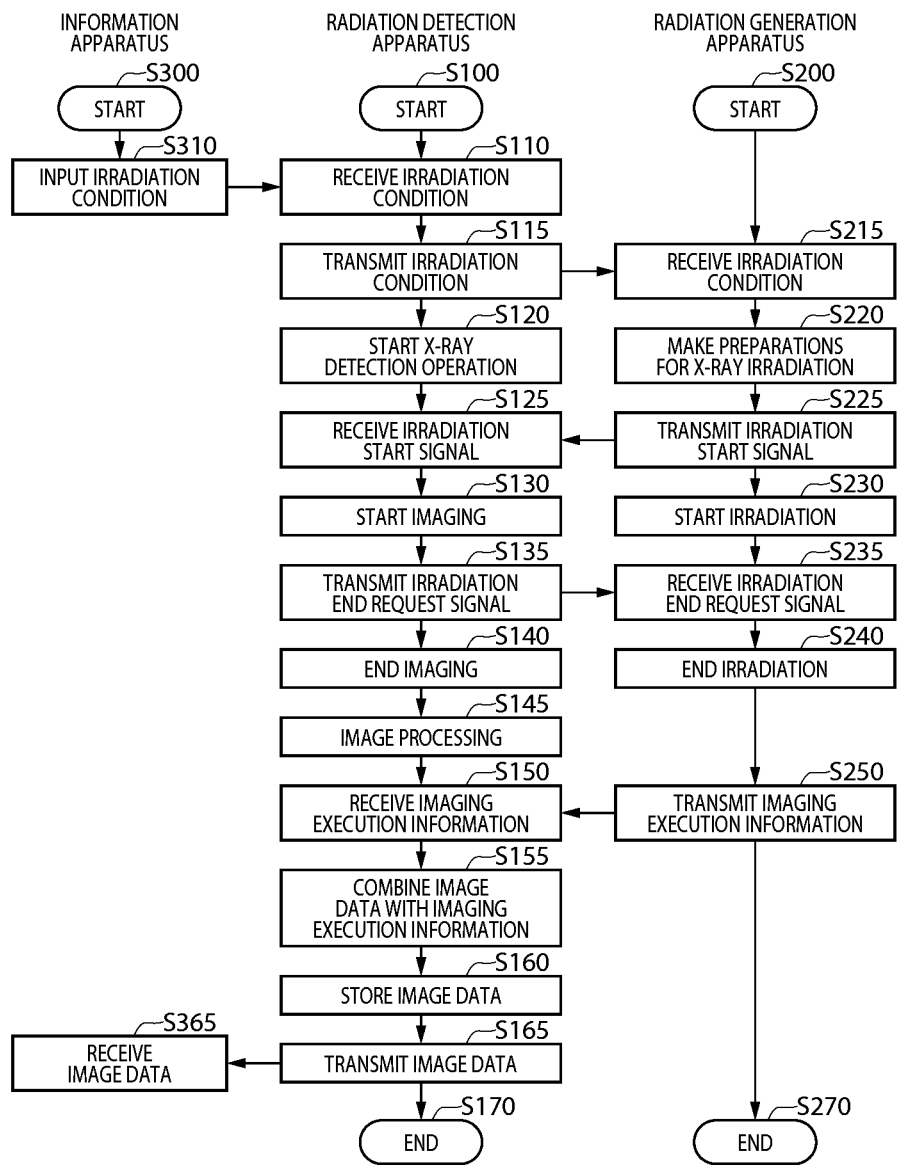

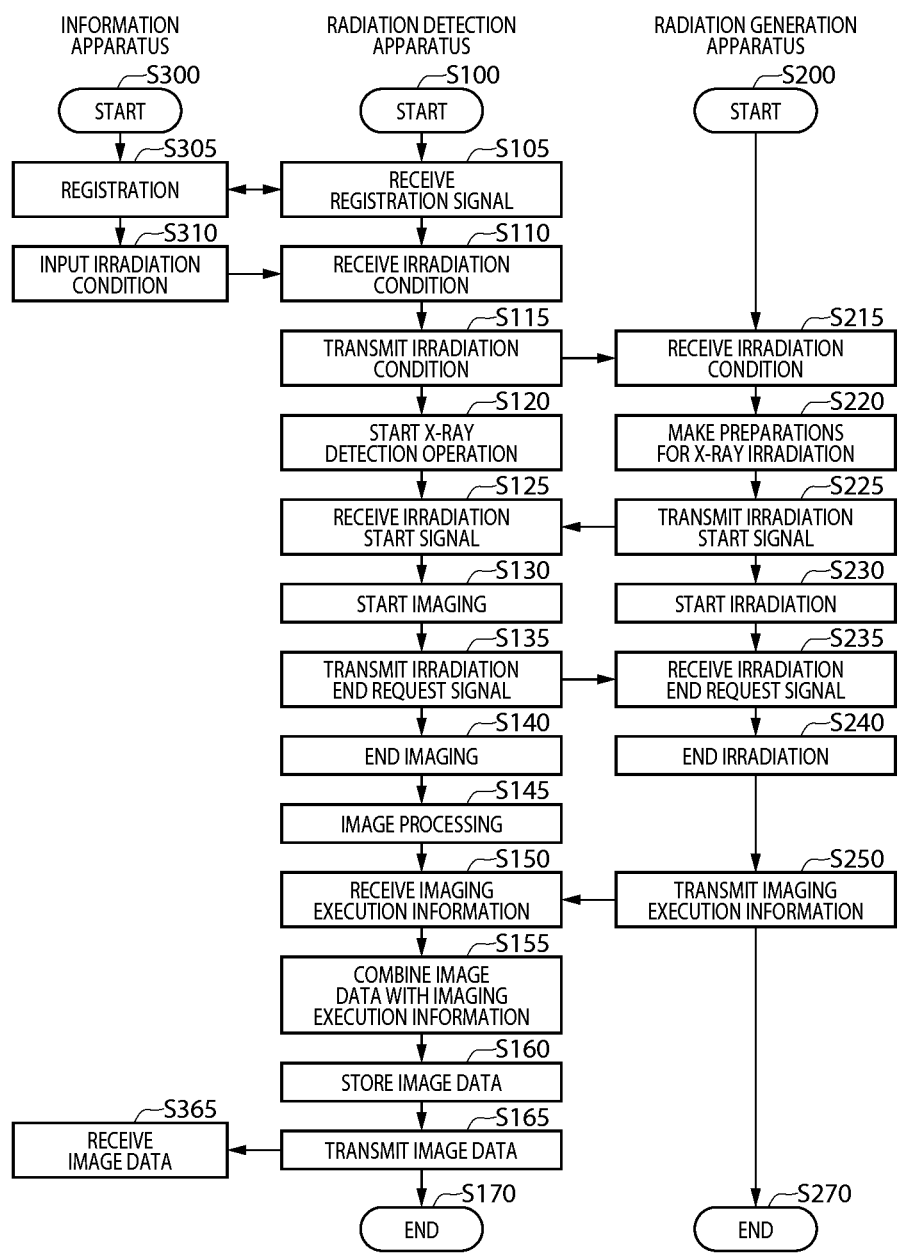

RADIATION IMAGING APPARATUS AND RADIATION IMAGING SYSTEM

BACKGROUND OF THE INVENTION

1. Field of the Invention

The present invention relates to a radiation imaging apparatus and a radiation imaging system.

2. Description of the Related Art

In recent years, more and more radiation images like medical X-ray images have been digitized. To capture a radiation digital image, a radiation imaging apparatus that uses, instead of a film, a plurality of radiation detection elements arranged in a two-dimensional matrix to convert a radiation into an electrical signal for image formation has been put to practical use. As an example of this type of radiation imaging apparatus, an X-ray detection apparatus (a flat panel detector (FPD)) has been discussed which includes a two-dimensional matrix of minute X-ray detectors each including a solid-state light detection element stacked on a scintillator that converts X-rays into visible light. The X-ray detection apparatus converts irradiated X-rays into an electrical signal corresponding to the exposure dose.

The digitization of an X-ray image by using an X-ray imaging apparatus including such an X-ray detection apparatus can provide various advantages. For example, the captured image can be immediately examined on a display device for faster diagnosis. Various types of image processing can be easily applied to automate diagnosis and improve the diagnostic accuracy of minute lesions. The absence of a need for a film storage space significantly improves the space efficiency in a hospital.

Little degradation of data during transmission further allows the captured image to be transmitted over a long distance without the degradation. Such a feature may be utilized, for example, to transmit an image captured in a home medical care setting or at a disaster site to a well-equipped urban hospital for a highly-trained doctor's diagnosis.

The system of such an X-ray imaging apparatus typically includes many components aside from an X-ray generation apparatus and an X-ray detection apparatus, including controllers for controlling the respective apparatuses, an image display unit like a display monitor, various interface devices for connecting the two apparatuses, and a large number of cables. For imaging, the X-ray generation apparatus and the X-ray detection apparatus exchange various types of information with each other. Examples include timing information for performing imaging in time with a start and end of X-ray irradiation. Such information is exchanged via various interface devices.

There has been discussed a method using an X-ray detection apparatus that can detect X-ray irradiation and perform imaging without exchanging a signal for adjusting irradiation timing between an X-ray generation apparatus and the X-ray detection apparatus. The use of such an X-ray detection apparatus can simplify the system components because interface devices for connecting the two apparatuses become unnecessary. In addition, a conventional visiting car, for example, that performs film-based imaging may be used to obtain digital images. In X-ray imaging, the management of X-ray doses with which patients are irradiated during imaging is essential. Japanese Patent Application Laid-Open No. 2000-107159 discusses that a control apparatus outside the detector associates image data with X-ray irradiation data.

The transmission of image data may include a gap from the transmission timing of irradiation data, for example, because of communication failure. In such cases, the image data and the irradiation data have sometimes failed to be reliably associated with each other.

Another problem is that the system where the X-ray generation apparatus and the X-ray detection apparatus exchange no irradiation timing includes no unit for communicating various types of information about irradiated X-rays to the X-ray detection apparatus. The various types of information here refer to imaging execution information including an X-ray tube voltage, an X-ray tube current, and irradiation time. The imaging execution information has conventionally been transmitted from the X-ray generation apparatus to a control apparatus and combined with image data transmitted from the X-ray detection apparatus. In contrast, the system where the X-ray generation apparatus and the X-ray detection apparatus exchange no such information has been unable to associate image data with imaging execution information, and sometimes caused a problem in the management of image data.

To address the foregoing problems, imaging execution information including an irradiation condition may be input and associated with image data by using a barcode or from a personal computer (PC). However, such a method entails an additional input operation and may give rise to an erroneous input of information. Setting values input to the X-ray generation apparatus may differ from an actual irradiation condition. Since a PC is needed as an input unit, there has also been the problem of increased system components.

SUMMARY OF THE INVENTION

According to an aspect of the present invention, a portable radiation imaging apparatus configured to wirelessly communicate with a radiation generation apparatus includes a radiation image sensor including a two-dimensional arrangement of a plurality of detection elements configured to detect a radiation generated by the radiation generation apparatus, a wireless communication unit configured to receive a generation condition of the radiation generated by the radiation generation apparatus, a storage unit configured to store the received generation condition and radiation image data obtained by the radiation image sensor in association with each other, and a housing configured to accommodate the radiation image sensor, the wireless communication unit, and the storage unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 6 is a flowchart illustrating an operation of the radiation imaging system according to the first exemplary embodiment.

FIG. 7 is a flowchart illustrating an operation of the radiation imaging system according to the second exemplary embodiment.

FIG. 8 is a flowchart illustrating an operation of the radiation imaging system according to the third exemplary embodiment.

FIG. 9 is another flowchart illustrating an operation of the radiation imaging system according to the third exemplary embodiment.

FIG. 10 is a flowchart illustrating an operation of the radiation imaging system according to the fourth exemplary embodiment.

FIG. 11 is a flowchart illustrating an operation of the radiation imaging system according to the fifth exemplary embodiment.

DESCRIPTION OF THE EMBODIMENTS

Various exemplary embodiments, features, and aspects of the invention will be described in detail below with reference to the drawings.

The following exemplary embodiments deal with a case where X-rays are used as the radiation. Similar effects of the exemplary embodiment of the present invention may be obtained even with other radiations including α rays, β rays, γ rays, and other electromagnetic waves.

Figure 1:
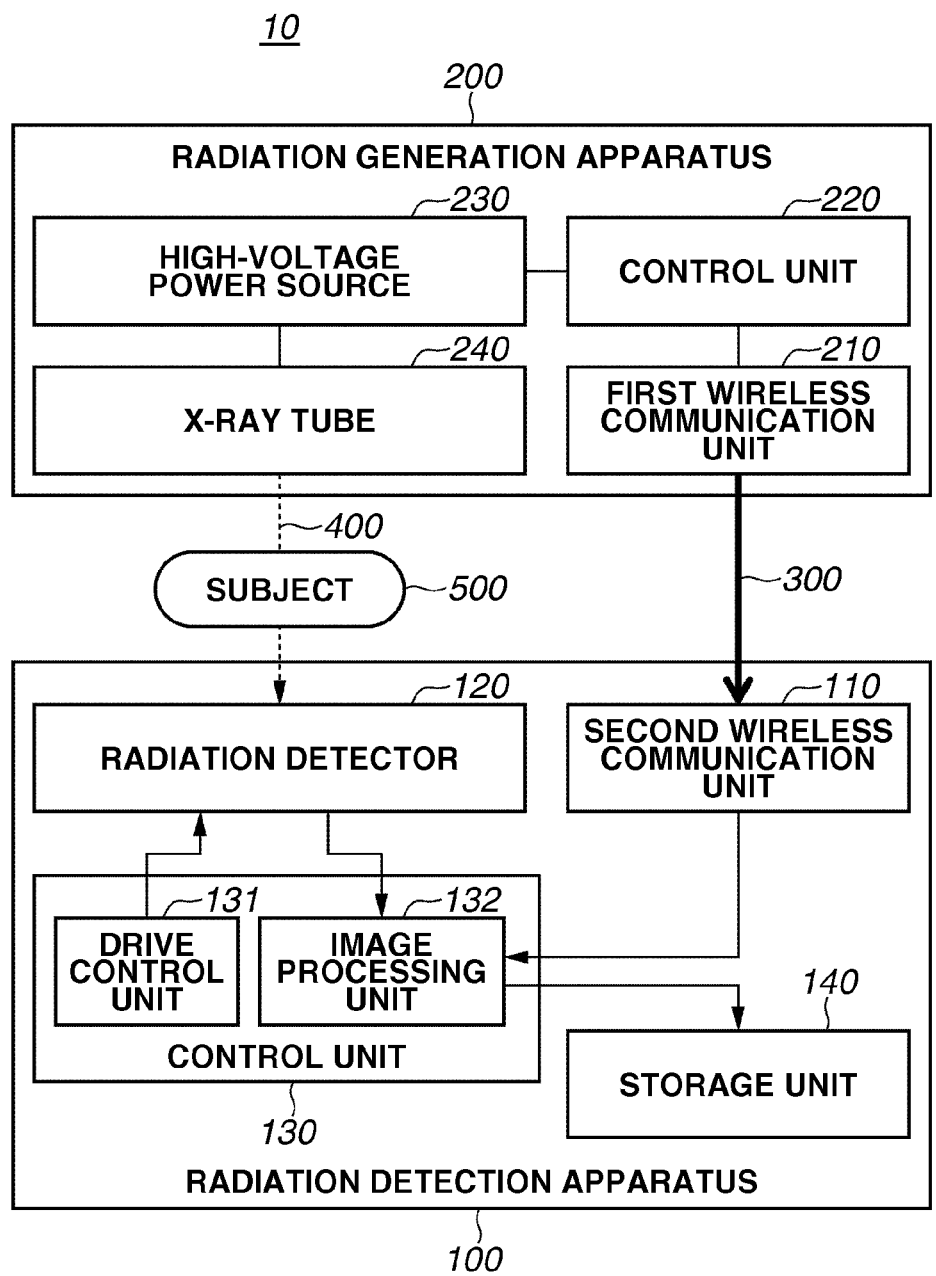
FIG. 1 is a diagram illustrating an example of a configuration of a radiation imaging system according to a first exemplary embodiment.

A first exemplary embodiment will be described below. FIG. 1 is a diagram illustrating an example of a configuration of a radiation imaging system 10 including a radiation detection apparatus 100 according to the first exemplary embodiment of the present invention. The radiation imaging system 10 includes the radiation detection apparatus 100 and a radiation generation apparatus 200. The radiation generation apparatus 200 irradiates a subject 500 with X-rays 400. A radiation detector 120 detects the X-rays 400 transmitted through the subject 500 to acquire X-ray image data.

The radiation generation apparatus 200 includes a control unit 220, a high-voltage power source 230, an X-ray tube 240, and a first wireless communication unit 210.

The first wireless communication unit 210 is used to input information from outside and output information from the radiation generation apparatus 200 by wireless communication. For example, the first wireless communication unit 210 can output imaging execution information. Examples of a wireless communication method to be used include a wireless local area network (LAN) and Bluetooth (registered trademark).

The control unit 220 controls the high-voltage power source 230 according to an input parameter or parameters about irradiating X-rays 400. A not-illustrated imaging condition input unit and/or irradiation start control unit may be connected to the control unit 220. As an example of the imaging condition input unit, the radiation generation apparatus 200 may include numerical input buttons and an input information display device. Alternatively, a keyboard or other input unit additionally connected to the radiation generation apparatus 200 may be used. X-ray irradiation is executed, for example, when a not-illustrated exposure button is pressed.

An example of the exposure button is a two-stage switch. If the exposure switch is pressed down to its first stage, the radiation generation apparatus 200 starts preparations for irradiation under a condition set by the control unit 220. If irradiation is ready and the exposure switch is pressed down to its second stage, the X-ray tube 240 emits X-rays 400.

The radiation detection apparatus 100 is a portable radiation imaging apparatus including the radiation detector 120, a control unit 130, a storage unit 140, a second wireless communication unit 110, and a housing for accommodating such components.

The second wireless communication unit 110 is capable of wireless communication with the first wireless communication unit 210. The second wireless communication unit 110 can transmit and receive various types of information. For example, the second wireless communication unit 110 receives a generation condition of X-rays 400 generated by the radiation generation apparatus 200 immediately after the generation of the X-rays 400.

The radiation detector 120 is a radiation image sensor that detects the X-rays 400 emitted from the X-ray tube 240 and transmitted through the subject 500. The radiation detector 120 includes a two-dimensional arrangement of a plurality of X-ray detection elements which generate electric charges according to the exposure dose of the X-rays 400. For example, the X-ray detection elements may be formed by laminating a pixel array and a phosphor, which emits light when irradiated with X-rays 400. The pixel array includes a two-dimensional matrix of a plurality of pixels each including a photoelectric conversion element and a thin-film transistor (TFT). Alternatively, conversion elements that directly generate charges from incident X-rays 400 may be used.

The control unit 130 includes a drive control unit 131 and an image processing unit 132. The drive control unit 131 controls driving of the radiation detector 120. The drive control unit 131 includes a central processing unit (CPU) for control, and operates to start and end acquisition of a radiation image and/or a correction image, read charges, and/or reset the radiation detector 120.

The image processing unit 132 makes corrections (including an offset correction and a defect correction) on read charge data of the radiation detector 120, forms a reduced image of the charge data, and associates the charge data with various types of data to form image data. The image processing unit 132 includes a programmable gate array (field programmable gate array (FPGA)) or a CPU, and a memory for primarily storing the image data. The FPGA or CPU may be common to the control unit 130. The various types of data include an imaging condition, patient information, and the imaging execution information.

The storage unit 140 stores various types of data including the generated image data. Examples of the storage unit 140 include a flash memory and a hard disk drive. While the storage unit 140 is arranged inside the radiation detection apparatus 100, the storage unit 140 may be configured to be detachable from the radiation detection apparatus 100. The storage unit 140 stores the received generation condition and radiation image data obtained by the radiation image sensor in association with each other.

FIG. 6 is a flowchart illustrating the radiation imaging system 10 according to the present first exemplary embodiment. An operation of the radiation imaging system 10 according to the present first exemplary embodiment will be described below with reference to FIG. 6.

In steps S100 and S200, the user makes both the radiation detection apparatus 100 and the radiation generation apparatus 200 start to operate. The radiation detection apparatus 100 and the radiation generation apparatus 200 each enter a preparation operation. In step S201, the user inputs an irradiation condition by using the input unit arranged on the radiation generation apparatus 200. The irradiation condition includes an X-ray tube voltage for the high-voltage power source 230 of the radiation generation apparatus 200 to output to be applied to the X-ray tube 240, an X-ray tube current, and/or irradiation time.

In step S220, the user presses the exposure button, such as a two-stage button, down to its first stage, and the radiation generation apparatus 200 makes preparations for X-ray irradiation.

In step S120, the radiation detection apparatus 100 starts an X-ray detection operation after a reset operation of the radiation detector 120, if needed. The X-ray detection operation includes detecting irradiation of the radiation detection apparatus 100 with the X-rays 400 and outputting a trigger for controlling the operation of the radiation detection apparatus 100.

In step S230, the user presses the exposure button down to the second stage, and the radiation generation apparatus 200 starts irradiation. If the radiation detection apparatus 100 detects the X-rays 400 (YES in step S127), then in step S130, the radiation detection apparatus 100 starts imaging.

In step S240, the radiation generation apparatus 200 ends irradiation. In step S140, the radiation detection apparatus 100 ends imaging. In step S145, the image processing unit 132 reads the imaged charge information and performs image processing to form image data. The image processing in step S145 includes various corrections (including an offset correction and a defect correction) and formation of a reduced image. The end of the imaging is controlled according to a preset X-ray accumulation time.

In step S250, after the end of the irradiation, the radiation generation apparatus 200 outputs imaging execution information 300 including an actual irradiation condition from the first wireless communication unit 210. In step S150, the second wireless communication unit 110 of the radiation detection apparatus 100 directly receives the imaging execution information 300. In step S155, the image processing unit 132 combines the image data with the received imaging execution information 300. In step S160, the resulting final image data is stored into the storage unit 140. In steps S170 and S270, the user ends the operation of the radiation detection apparatus 100 and the radiation generation apparatus 200.

Since the radiation detection apparatus 100 directly receives the imaging execution information 300 from the radiation generation apparatus 200 and combines the image data with the received imaging execution information 300, the image data and the imaging execution information 300 can be reliably associated with each other. This may avoid confusion about image management.

Figure 2:
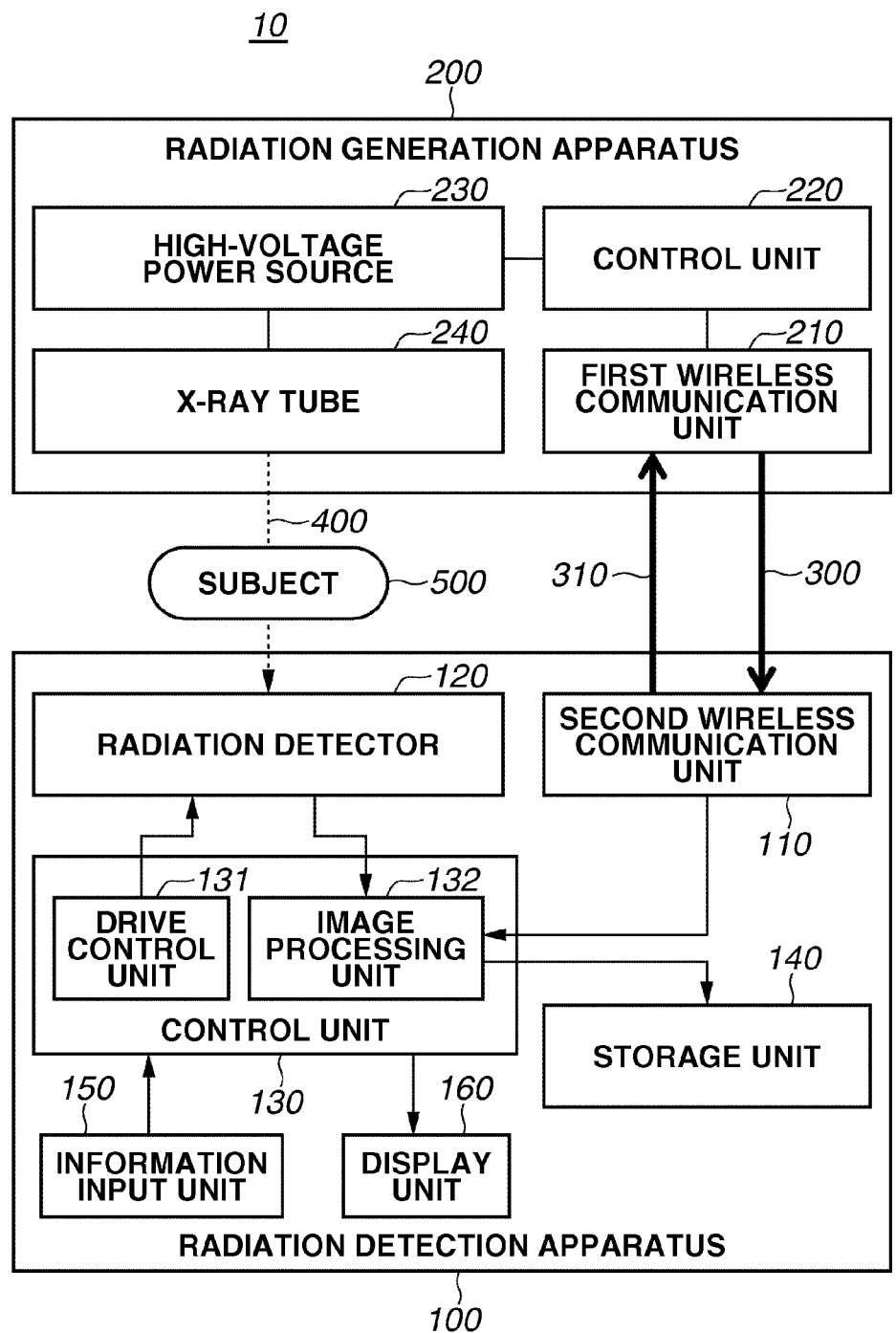
FIG. 2 is a diagram illustrating an example of a configuration of a radiation imaging system according to a second exemplary embodiment.

A second exemplary embodiment will be described below. FIG. 2 is a diagram illustrating an example of a configuration of a radiation imaging system 10 including a radiation detection apparatus 100 according to the second exemplary embodiment of the present invention. In the present second exemplary embodiment, an information input unit 150 and a display unit 160 are added to the inside of the radiation detection apparatus 100 of the first exemplary embodiment.

The information input unit 150 is intended to input numerical values and characters. The information input unit 150 may be used to input patient information and an imaging condition, and/or switch operation modes of the radiation detection apparatus 100. The information input unit 150 may include switches, dials, and/or a touch panel. Information may be input by directly entering characters and/or by selecting previously-input information.

In the present exemplary embodiment, the radiation detection apparatus 100 and the radiation generation apparatus 200 directly communicate an irradiation condition as well as imaging execution information with each other by wireless communication. The user inputs an irradiation condition to the radiation detection apparatus 100, and the radiation direction apparatus 100 directly transmits the input irradiation condition 310 to the radiation generation apparatus 200 by wireless communication, whereby the irradiation condition 310 is set. An X-ray image and the irradiation condition 310 can thus be reliably associated with each other. Since the end timing of irradiation can be estimated from a set irradiation time, the radiation detection apparatus 100 can perform imaging with an appropriate X-ray accumulation time according to the irradiation time. This can improve the image quality of the X-ray image data.

The display unit 160 is intended to display characters and/or image information. Examples of the display unit 160 include a liquid crystal panel and an organic electroluminescence (EL) panel. The display unit 160 can display various types of information input from the information input unit 150, imaging execution information 300 transmitted from the radiation generation apparatus 200, and information about an operation status of the radiation detector 120. The display unit 160 may be used to display a captured radiation image.

FIG. 7 is a flowchart illustrating the radiation imaging system 10 according to the present second exemplary embodiment. An operation of the radiation imaging system according to the second exemplary embodiment will be described below with a focus on differences from the first exemplary embodiment.

In step S101, after the start of the operation of the radiation generation apparatus 200 and the radiation detection apparatus 100, the user inputs an irradiation condition 310 by using the information input unit 150 of the radiation detection apparatus 100. The irradiation condition 310 to be input here includes the X-ray tube voltage, X-ray tube current, and irradiation time of the radiation generation apparatus 200. Numerical values may be individually specified. Values may be selected from preset values stored in the radiation detection apparatus 100 in advance.

In step S115, according to the second exemplary embodiment, the radiation detection apparatus 100 transmits the input irradiation condition 310 via the control unit 130 from the second wireless communication unit 110 to the radiation generation apparatus 200. In step S215, the first wireless communication unit 210 of the radiation generation apparatus 200 receives the transmitted irradiation condition 310. The radiation generation apparatus 200 then makes preparations for irradiation and performs X-ray irradiation. The imaging flow up to the start of imaging is similar to that of the first exemplary embodiment. A description thereof is thus not repeated.

Upon detecting the X-ray irradiation, the radiation detection apparatus 100 starts imaging. The radiation detection apparatus 100 measures elapsed time since the start of the imaging. In step S140, the radiation detection apparatus 100 ends imaging at timing when the elapsed time exceeds the irradiation time set in step S101.

The radiation detection apparatus 100 may store the input irradiation condition 310 into the storage unit 140. The stored irradiation condition 310 can be associated with a captured image to add various types of information to the image data aside from the imaging execution information 300 directly transmitted from the radiation generation apparatus 200. This facilitates image management.

Figure 3:
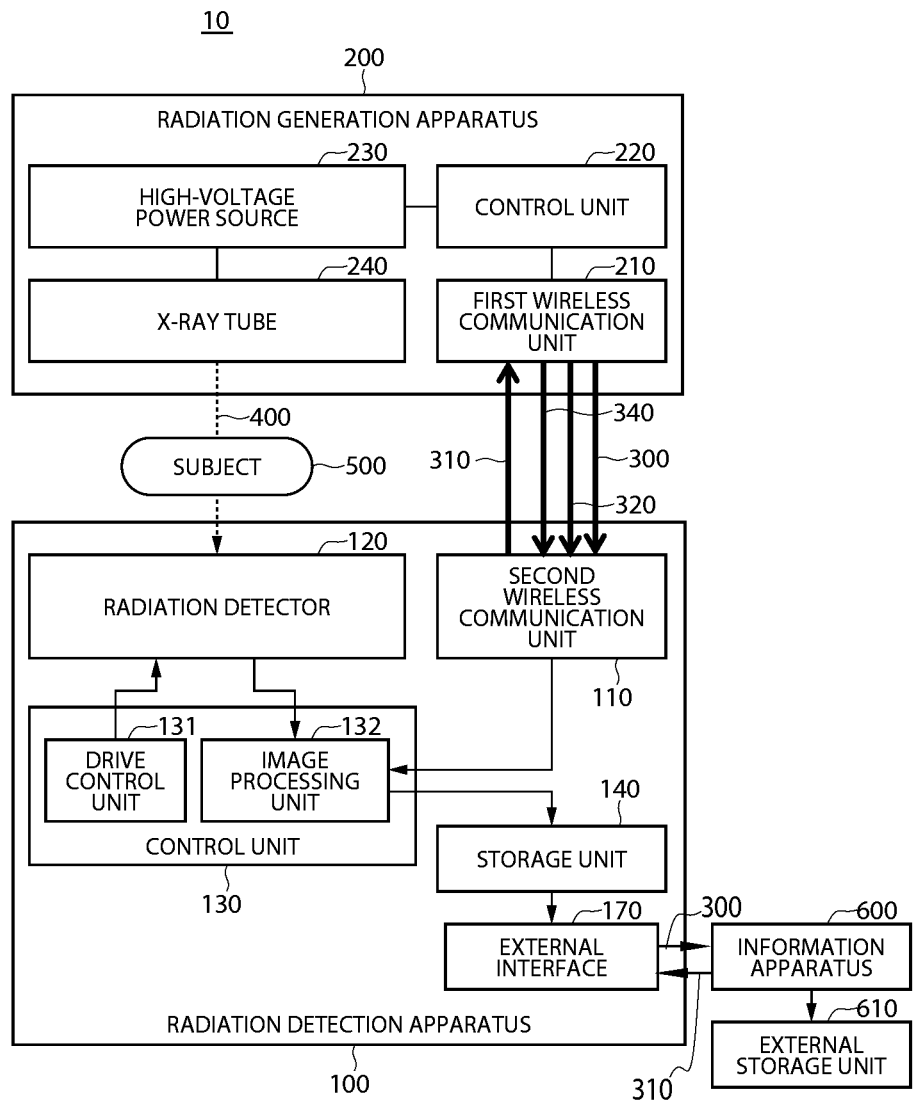
FIG. 3 is a diagram illustrating an example of a configuration of a radiation imaging system according to a third exemplary embodiment.

A third exemplary embodiment will be described below. FIG. 3 is a diagram illustrating an example of a configuration of a radiation imaging system 10 including a radiation detection apparatus 100 according to the third exemplary embodiment of the present invention. The present third exemplary embodiment includes an external interface 170, which is added to the radiation detection apparatus 100 of the first exemplary embodiment. An external information apparatus 600 is connected to the radiation detection apparatus 100.

A general-purpose interface such as a universal serial bus (USB) flash drive and Recommended Standard 232 C (RS-232-C) may be suitably used as the external interface 170. An Ethernet or other network communication port may be used. A dedicated interface may be provided.

The information apparatus 600 is connected to the external interface 170. Examples of the information apparatus 600 include a personal computer (PC), a tablet PC, and a workstation. Any device that can input necessary information and communicate with the radiation detection apparatus 100 may be used. The information apparatus 600 includes an internal storage unit (not illustrated) and can store various types of information. Examples of the internal storage unit include a hard disk drive, a flash memory, and various types of optical disk writing devices.

An external storage unit 610 may be connected to the information apparatus 600. Examples of the external storage unit 610 include a hard disk drive, a flash memory, various types of optical disk writing devices, and various servers and database apparatuses.

FIG. 8 is a flowchart illustrating the radiation imaging system 10 according to the present third exemplary embodiment. An operation of the radiation imaging system according to the third exemplary embodiment will be described below with a focus on differences from the first exemplary embodiment.

In steps S100, S200, and S300, the user makes the radiation detection apparatus 100, the radiation generation apparatus 200, and the information apparatus 600 start to operate. The order of starting operations is not limited in particular. The operation of the radiation generation apparatus 200 need not be started at this stage.

In step S310, the user inputs an irradiation condition 310 to the information apparatus 600. The irradiation condition 310 refers to a condition including an X-ray tube voltage, an X-ray tube current, and irradiation time. Numerical values may be individually input. Desired values may be selected from a condition table prepared in advance. The user inputs the irradiation condition 310 by using an input unit connected to the information apparatus 600, such as a keyboard (not illustrated) and a touch panel (not illustrated).

In step S310, after the completion of the input, the information apparatus 600 transmits the irradiation condition 310 to the radiation detection apparatus 100. The information apparatus 600 may transmit all the irradiation condition 310 at a time after the completion of the input, or may transmit individual pieces of input irradiation condition 310 in order. In step S110, the radiation detection apparatus 100 receives the irradiation condition 310. The radiation detection apparatus 100 stores the irradiation condition 310 into the storage unit 140. In steps S115 and S215, the second wireless communication unit 110 of the radiation detection apparatus 100 transmits the irradiation condition 310 to the first wireless communication unit 210 of the radiation generation apparatus 200. The subsequent flow of the X-ray irradiation and imaging is similar to that of the second exemplary embodiment.

In step S140, the radiation detection apparatus 100 ends imaging at timing when the elapsed time since the time of detection of the X-ray irradiation exceeds the irradiation time input in step S310.

The radiation generation apparatus 200 and the radiation detection apparatus 100 may directly exchange a synchronization signal for synchronizing irradiation timing and imaging timing with each other along with the imaging execution information 300 and the irradiation condition 310. FIG. 9 is a flowchart illustrating the imaging of such a radiation imaging system 10. In step S225, the radiation generation apparatus 200 transmits an irradiation start signal 320 to the radiation detection apparatus 100 by wireless communication immediately before the timing when the radiation generation apparatus 200 completes preparations and starts irradiation. In step S125, the radiation detection apparatus 100 receives the irradiation start signal 320. In step S130, the radiation detection apparatus 100 immediately starts imaging. The radiation generation apparatus 200 performs irradiation according to the irradiation time set in step S310. In step S244, after the end of the irradiation, the radiation generation apparatus 200 transmits an irradiation end signal 340 to the radiation detection apparatus 100 by wireless communication. In step S134, the radiation detection apparatus 100 receives the irradiation end signal 340. In step S140, the radiation detection apparatus 100 ends imaging.

Receiving the irradiation start signal 320, the radiation detection apparatus 100 may transmits an irradiation enable signal to the radiation generation apparatus 200 when the radiation detection apparatus 100 becomes ready for imaging. In such a case, X-ray irradiation may be disabled until the reception of the irradiation enable signal, whereby accidental X-ray irradiation and exposure may be avoided.

After the end of the imaging, the radiation detection apparatus 100 stores the image data associated with the imaging execution information 300 directly transmitted from the radiation generation apparatus 200 into the storage unit 140. In step S165, the radiation detection apparatus 100 transmits the image data to the information apparatus 600 connected via the external interface 170. In step S365, the information apparatus 600 receives the transmitted image data, and performs various types of processing. For example, the information apparatus 600 may store the image data into the connected external storage unit 610. The information apparatus 600 may apply various types of sophisticated image processing to the image data. The information apparatus 600 may further display such a processed image on a not-illustrated image display device, or output the image to a not-illustrated printer. If the information apparatus 600 is connected to a network, the image data may be shared within the network for enhanced convenience.

Figure 4:
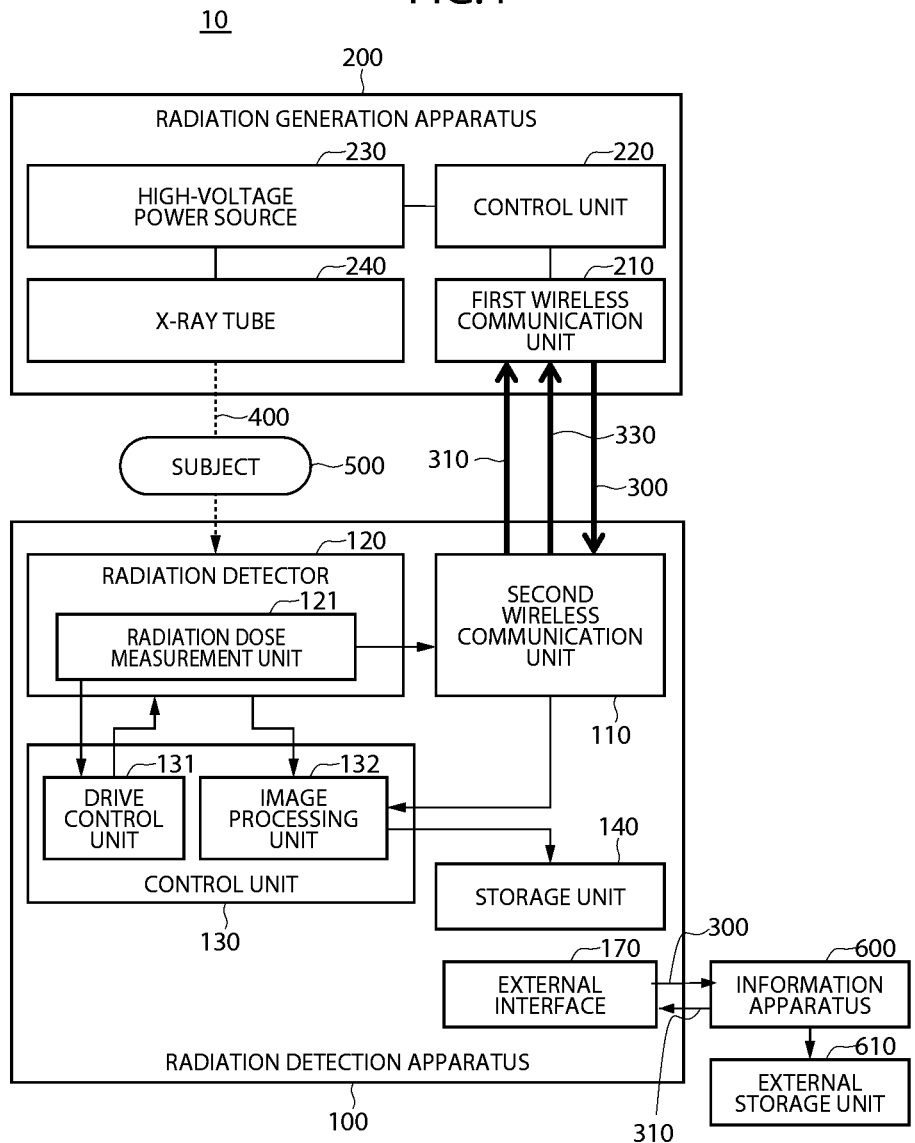
FIG. 4 is a diagram illustrating an example of a configuration of a radiation imaging system according to a fourth exemplary embodiment.

A fourth exemplary embodiment will be described below. FIG. 4 is a diagram illustrating an example of a configuration of a radiation imaging system 10 including a radiation detection apparatus 100 according to the fourth exemplary embodiment of the present invention. The present fourth exemplary embodiment includes a radiation dose measurement unit 121, which is added to the radiation detection device 100 of the third exemplary embodiment.

The radiation dose measurement unit 121 is intended to measure the total exposure dose of the irradiated radiation. The radiation dose measurement unit 121 has a function of making a notification when the total exposure dose has reached an exposure dose needed for image formation. Ending the imaging and stopping the irradiation according to the notification timing may achieve both satisfactory image quality and reduced exposure at the same time. The radiation dose measurement unit 121 may include a dedicated detector. A part of the radiation detector 120 for image acquisition may be used to constitute the radiation dose measurement unit 121.

FIG. 10 is a flowchart illustrating the radiation imaging system 10 according to the present fourth exemplary embodiment. An operation of the radiation imaging system according to the fourth exemplary embodiment will be described below with a focus on differences from the third exemplary embodiment.

In step S310, the information apparatus 600 transmits an input irradiation condition 310 to the radiation detection apparatus 100. In step S115, the radiation detection apparatus 100 transmits the irradiation condition 310 to the radiation generation apparatus 200. According to the set irradiation condition 310, the radiation generation apparatus 200 performs X-ray irradiation for the set irradiation time.

While the radiation detection apparatus 100 performs imaging, the radiation dose measurement unit 121 measures the total exposure dose of the X-rays 400. If the measured exposure dose has reached a setting value, which can be arbitrarily set, then in step S135, the radiation detection apparatus 100 transmits an irradiation end request signal 330 to the radiation generation apparatus 200. In step S140, the radiation detection apparatus 100 ends imaging. The radiation detection apparatus 100 may store information about the elapsed time since the start of the imaging and the exposure dose. In step S235, the radiation generation apparatus 200 receives the irradiation end request signal 330. In step S240, the radiation generation apparatus 200 immediately ends irradiation.

The flow after the end of the irradiation is similar to that of the third exemplary embodiment.

Figure 5:
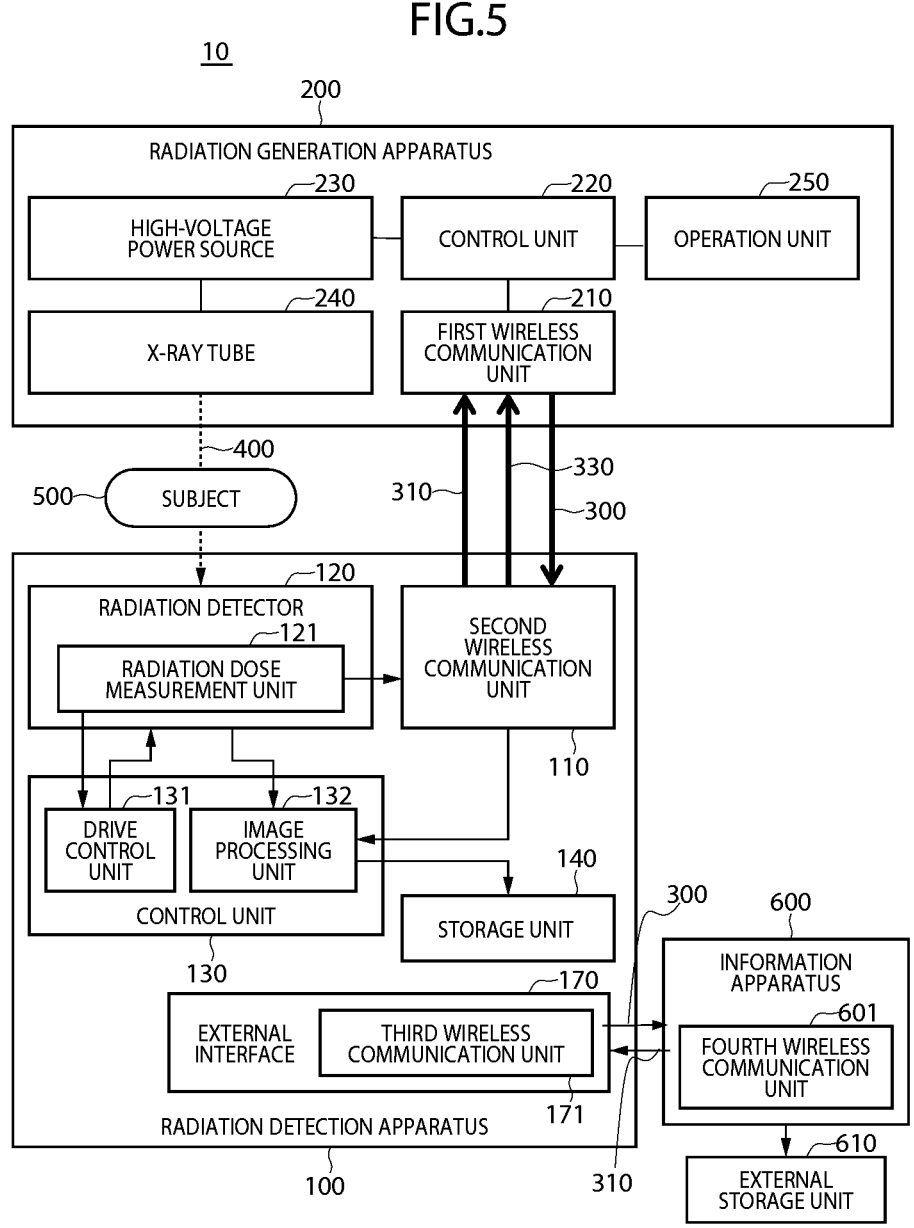
FIG. 5 is a diagram illustrating an example of a configuration of a radiation imaging system according to a fifth exemplary embodiment.

A fifth exemplary embodiment will be described below. FIG. 5 is a diagram illustrating an example of a configuration of a radiation imaging system 10 including a radiation detection apparatus 100 according to the fifth exemplary embodiment of the present invention. The present fifth exemplary embodiment includes a third wireless communication unit 171, which is added to the fourth exemplary embodiment as an external interface of the radiation detection apparatus 100.

The third wireless communication unit 171 may use a wireless LAN, Bluetooth (registered trademark), and/or infrared communications. The third wireless communication unit 171 uses a frequency band and/or a communication unit different from those of the first and second wireless communication units 210 and 110. If the first, second, and third wireless communication units 210, 110, and 171 all use a wireless LAN of the same standard of the Institute of Electrical and Electronics Engineers (IEEE) 802.11 series, different service set identifiers (SSIDs) are assigned thereto.

In the fifth exemplary embodiment, an information apparatus 600 including a fourth wireless communication unit 601 is connected to the radiation detection apparatus 100. Examples of the information apparatus 600 include a notebook PC and a tablet PC. A workstation may be suitably used. There may be a plurality of information apparatuses 600 like when a plurality of operators owns their respective tablet PCs or notebook PCs.

According to the present exemplary embodiment, an environment where the radiation detection apparatus 100 can be operated from a plurality of information apparatuses 600 can be conveniently constructed.

FIG. 11 is a flowchart illustrating the radiation imaging system 10 according to the present fifth exemplary embodiment. An operation of the radiation imaging system according to the fifth exemplary embodiment will be described below with a focus on differences from the fourth exemplary embodiment.

In steps S100, S200, and S300, the user makes the radiation detection apparatus 100, the radiation generation apparatus 200, and the information apparatus 600 start to operate. In S305, the user performs a registration operation for establishing connection from the information apparatus 600, which is to be connected to the radiation detection apparatus 100.

A method for connecting a specific information apparatus 600 to the radiation detection apparatus 100 will be described below.

The third wireless communication unit 171 of the radiation detection apparatus 100 has a unique identifier. Examples include an SSID of an IEEE 802.11 series wireless LAN. A Wi-Fi Protected Access (WPA) or WPA2 pre-shared key (PSK) may be used. The information apparatus 600 attempting connection to the radiation detection apparatus 100 inputs the SSID, PSK, or other identifier, and is thus connected to the radiation detection apparatus 100. A desired identifier may be selected from a plurality of connectable identifiers. The thus connected information apparatus 600 can be used to input information to the radiation detection apparatus 100 and/or control the acquisition of data.

The radiation detection apparatus 100 connected with an arbitrary information apparatus 600 is not connectable to other information apparatuses 600. Such a state is maintained until a disconnecting procedure is performed on the connected information apparatus 600. The information apparatus 600 may be automatically disconnected if unoperated for a certain time. After disconnection, a connectable information apparatus 600 can be newly connected for use.

In step S310, the user inputs an irradiation condition 310 from the information apparatus 600 connected thus, and the radiation imaging system 10 performs imaging. The flow after the input of the irradiation condition 310 is similar to that of the fourth exemplary embodiment. A description thereof is thus not repeated.

The provision of the third wireless communication unit 170 enables connection with an arbitrary information apparatus 600, from which the radiation detection apparatus 100 can be controlled. Besides, the radiation detection apparatus 100 can directly receive imaging execution information 300 from the radiation generation apparatus 200 and combine image data with the imaging execution information 300 to reliably associate the image data with the imaging execution information 300. Confusion about image management may thus be avoided.

According to the foregoing exemplary embodiments, the radiation detection apparatus 100 receives subject information and information about an imaging portion from the information apparatus 600. However, this is not restrictive. The radiation detection apparatus 100 may receive such information from the radiation generation apparatus 200 along with the imaging execution information 300. For example, the radiation generation apparatus 200 may have a function of receiving an imaging order from a radiology information system (RIS). The radiation generation apparatus 200 then sets a generation condition by using information included in the imaging order, such as subject information, information about an imaging portion, and information about a prescribed generation condition. The user may operate an operation unit 250 of the radiation generation apparatus 200 to arbitrarily change the generation condition including an X-ray tube current, an X-ray tube voltage, and a current time product (mAs) value. The radiation generation apparatus 200 may set a generation condition by referring to a standard generation condition that is stored in association with information about an imaging portion and subject information such as an age.

Using the set generation condition, the radiation generation apparatus 200 generates X-rays 400. In the presence of an auto exposure control (AEC), a subject 500 may be irradiated only with a dose of X-rays 400 smaller than the set value. This causes a discrepancy between the set generation condition and a generation condition as execution result information under which the X-rays 400 has been actually generated. The radiation generation apparatus 200 transmits the generation condition as the execution result information to the radiation detection apparatus 100 (a radiation imaging apparatus). It will be understood that the radiation generation apparatus 200 may also transmit a generation condition set before the imaging and a determined prescribed generation condition based on the imaging portion to the radiation detection apparatus 100. The transmission of such conditions is useful because differences among the prescribed condition, the set condition, and the condition of the actual radiation generation may be determined.

The radiation generation apparatus 200 may further transmit the subject information and the information about the imaging portion to the radiation detection apparatus 100, and the radiation detection apparatus 100 may store such information in association with an image and the generation condition. This allows appropriate association among the information of the imaging order, the generation condition, and the radiation image data.

Suppose that the radiation generation apparatus 200 is configured to transmit the imaging execution information 300, the subject information, and the information about the imaging portion to the radiation detection apparatus 100. Since the number of pieces of data is small, the radiation generation apparatus 200 and the radiation detection apparatus 100 normally finish the communication immediately after the generation of the X-rays 400. The transmission may sometimes take a long time, however, because of a communication problem. The radiation detection apparatus 100 may be configured to disable subsequent imaging if the radiation detection apparatus 100 fails to receive the information supposed to be received from the radiation generation apparatus 200. This may reliably associate an image with its accessory information.

In another example, before each imaging operation, the radiation detection apparatus 100 and the radiation generation apparatus 200 may share ID information about the subsequent imaging to solve the association problem. For example, an ID included in an imaging order, defined for each single imaging operation, is transmitted from the information apparatus 600 or the radiation generation apparatus 200 to the radiation detection apparatus 100, so that the radiation generation apparatus 200 and the radiation detection apparatus 100 store and share the ID in their respective storage units. Consequently, even if the radiation generation apparatus 200 and the radiation detection apparatus 100 become unable to communicate imaging execution information 300 because of a communication problem after imaging, the ID information enables and secures association between image information and its accessory information.

The radiation generation apparatus 200 may transmit the actual X-ray generation condition to the radiation detection apparatus 100 in response to a request from the radiation detection apparatus 100. Such timing may reduce the possibility of a timeout when transmitting the X-ray generation condition, for example, if the radiation detection apparatus 100 suspends its wireless communication function during image reading. A monitoring function of monitoring the quality of wireless communication by using a received signal strength indicator (RSSI) may be implemented in the radiation detection apparatus 100 or other locations of the radiation imaging system 10, so that the radiation detection apparatus 200 can transmit imaging execution information 300 when the quality of the wireless communication is higher than a certain level. This can reduce the possibility of a communication timeout, for example, due to noise resulting from X-ray generation.

The radiation detection apparatus 100 may transmit, for example, a reduced image, a thinned image, or a partial image of the captured radiation image data to the external information apparatus 600 and/or the radiation generation apparatus 200 before or after the timing when the image and accessory information are associated with each other. This allows the user to examine the captured image at earlier timing without waiting for the association of the captured image and the accessory information.

As has been described above, according to the foregoing exemplary embodiments, the radiation generation apparatus 200 and the radiation detection apparatus 100 can conveniently and reliably associate captured image data and imaging execution information 300 about the irradiated X-rays 400 without additional operations. This may avoid confusion about image management.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-096099 filed Apr. 19, 2012, which is hereby incorporated by reference herein in its entirety.

What is claimed is:

1. A portable radiation imaging apparatus configured to wirelessly communicate with a radiation generation apparatus, the portable radiation imaging apparatus comprising:
   a radiation image sensor including a two-dimensional arrangement of a plurality of detection elements configured to detect a radiation generated by the radiation generation apparatus;
   a wireless communication unit configured to receive a generation condition of the radiation generated by the radiation generation apparatus;

a control unit configured to associate the received generation condition and radiation image data obtained by the radiation image sensor;

a storage unit configured to store the received generation condition and radiation image data associated by the control unit; and a housing configured to accommodate the radiation image sensor, the wireless communication unit, and the storage unit.

2. The portable radiation imaging apparatus according to claim 1, wherein the wireless communication unit is configured to receive the generation condition from the radiation generation apparatus after generation of the radiation.

3. The portable radiation imaging apparatus according to claim 1, wherein the wireless communication unit is configured to transmit the stored radiation image data to a terminal apparatus along with the generation condition.

4. The portable radiation imaging apparatus according to claim 1, wherein the wireless communication unit is configured to receive subject information corresponding to the radiation image data from the radiation generation apparatus along with the generation condition, and wherein the storage unit is configured to store the radiation image data, the subject information, the generation condition, and association information that associates the radiation image data, the subject information, and the generation condition.

5. A radiation imaging system comprising:

a radiation generation apparatus including a first wireless communication unit; and a radiation detection apparatus including a second wireless communication unit capable of wireless communication with the first wireless communication unit, wherein the radiation generation apparatus and the radiation detection apparatus are configured to directly exchange information by wireless communication, wherein the radiation detection apparatus includes a single housing, a storage unit and a control unit in the housing, wherein the radiation generation apparatus is configured to transmit information with regard to a generation condition of the radiation to the radiation detection apparatus after irradiation with a radiation, wherein the control unit is configured to associate a captured radiation irradiation image with the information with regard to a generation condition of the radiation and to generate image data, and wherein the radiation detection apparatus is configured to store the image data into the storage unit.

6. The radiation imaging system according to claim 5, wherein the radiation detection apparatus includes a single housing, and wherein the second wireless communication unit and the storage unit are arranged in the housing.

7. The radiation imaging system according to claim 5, wherein the radiation detection apparatus includes an information input unit and a display unit.

8. The radiation imaging system according to claim 7, wherein the radiation detection apparatus is configured to be capable of inputting an imaging condition from the information input unit, and to store the input imaging condition into the storage unit.

9. The radiation imaging system according to claim 5, wherein the radiation detection apparatus includes an external interface.

10. The radiation imaging system according to claim 9, wherein the radiation detection apparatus is connectable with an information apparatus such as a PC via the external interface.

11. The radiation imaging system according to claim 9, wherein the information apparatus is configured to transmit an imaging condition to the radiation detection apparatus, and wherein the radiation detection apparatus is configured to store the transmitted imaging condition into the storage unit.

12. The radiation imaging system according to claim 5, wherein the radiation detection apparatus is configured to transmit an imaging condition stored in the storage unit to the radiation generation apparatus before imaging of a radiation image.

13. The radiation imaging system according to claim 5, wherein the radiation generation apparatus is configured to generate a radiation based on an imaging condition.

14. The radiation imaging system according to claim 5, wherein the radiation detection apparatus is configured to transmit the image data stored in the storage unit to an information apparatus.

15. The radiation imaging system according to claim 5, wherein the information exchanged between the radiation generation apparatus and the radiation detection apparatus includes an imaging condition, the imaging execution information, and a synchronization signal regarding radiation irradiation and imaging.

16. The radiation imaging system according to claim 15, wherein the synchronization signal is a signal used to notify the radiation detection apparatus of start timing of the irradiation with the radiation from the radiation generation apparatus.

17. The radiation imaging system according to claim 15, wherein the synchronization signal is a signal used for the radiation generation apparatus to notify the radiation detection apparatus of an end of the irradiation with the radiation.

18. The radiation imaging system according to claim 5, wherein the radiation detection apparatus includes a radiation measurement unit configured to measure a total exposure dose of the radiation.

19. The radiation imaging system according to claim 18, wherein a synchronization signal is a signal used for the radiation detection apparatus to request the radiation generation apparatus to end the irradiation with the radiation based on the total exposure dose of the radiation measured by the radiation measurement unit.

20. The radiation imaging system according to claim 19, wherein the radiation generation apparatus is configured to transmit the imaging execution information to the radiation detection apparatus after transmission of the signal for requesting the end of the irradiation with the radiation.

21. The radiation imaging system according to claim 5, wherein the radiation generation apparatus includes a portable radiation generation apparatus.

22. The radiation imaging system according to claim 5, wherein the first and second wireless communication units include short-range wireless communication units.

23. The radiation imaging system according to claim 5, wherein the radiation detection apparatus further includes a third wireless communication unit as an external interface, wherein the radiation imaging system includes a unit configured to receive a registration signal from a terminal apparatus among a plurality of terminal apparatuses connectable to the radiation detection apparatus by the third wireless communication unit, and to register the terminal apparatus, wherein the radiation detection apparatus is configured to receive an imaging condition from the registered terminal apparatus, and wherein the radiation detection apparatus is configured to transmit the image data stored in the storage unit to the registered terminal apparatus.

24. The radiation imaging system according to claim 23, wherein an SSID different from those of the first and second wireless communication units is assigned to the third wireless communication unit.

25. The radiation imaging system according to claim 5, wherein the information with regard to a generation condition of the radiation includes at least one of a tube voltage, a tube current, and irradiation time.

* * * * *